United States Patent [19]

Kraft et al.

[11] 4,281,387

[45] Jul. 28, 1981

[54] AUTOMATIC CHEMICAL ANALYSIS APPARATUS AND METHOD

[75] Inventors: Thomas L. Kraft; Howard A. Vick, both of Houston, Tex.; Miles G. Hossom, Hauppauge, N.Y.

[73] Assignee: American Home Products Corp., New York, N.Y.

[21] Appl. No.: 40,524

[22] Filed: May 21, 1979

[51] Int. Cl.³ .................. G06F 15/20; G01N 33/16
[52] U.S. Cl. ..................... 364/497; 422/67; 422/62; 356/319
[58] Field of Search ............ 364/497, 499, 416; 422/67; 23/259; 356/39, 246, 319, 326

[56] References Cited

U.S. PATENT DOCUMENTS

| | | | |
|---|---|---|---|
| 3,621,215 | 11/1971 | Netheler et al. | 364/579 |
| 3,691,364 | 9/1972 | Baba et al. | 364/497 |
| 3,728,080 | 4/1973 | Moran | 364/499 X |
| 3,748,044 | 7/1973 | Liston | 364/497 X |
| 3,775,595 | 11/1973 | Rosse et al. | 364/497 X |
| 3,832,135 | 8/1974 | Drozdowski et al. | 364/497 X |
| 3,860,393 | 1/1975 | Campen, Jr. | 364/497 X |
| 4,115,861 | 9/1978 | Allington | 364/497 |
| 4,133,642 | 1/1979 | Nosaka et al. | 422/67 |
| 4,158,545 | 1/1979 | Yamashita et al. | 364/497 X |
| 4,166,095 | 8/1979 | Kling et al. | 364/497 X |

*Primary Examiner*—Edward J. Wise
*Attorney, Agent, or Firm*—Eugene L. Flanagan, III

[57] ABSTRACT

Automated chemical analysis apparatus is disclosed for testing a plurality of chemical samples in variable testing sequences. In the preferred embodiment, the apparatus is operative to test bacterial sensitivity to a plurality of drugs, each of which may have varying concentrations. More specifically, one, two or three concentrations of each of a plurality of drugs may be tested in accordance with sequence command information on a source/record card which is automatically entered into the apparatus. The results of the variable sequence testing are recorded directly on the card adjacent to the identification of the drug being tested.

45 Claims, 11 Drawing Figures

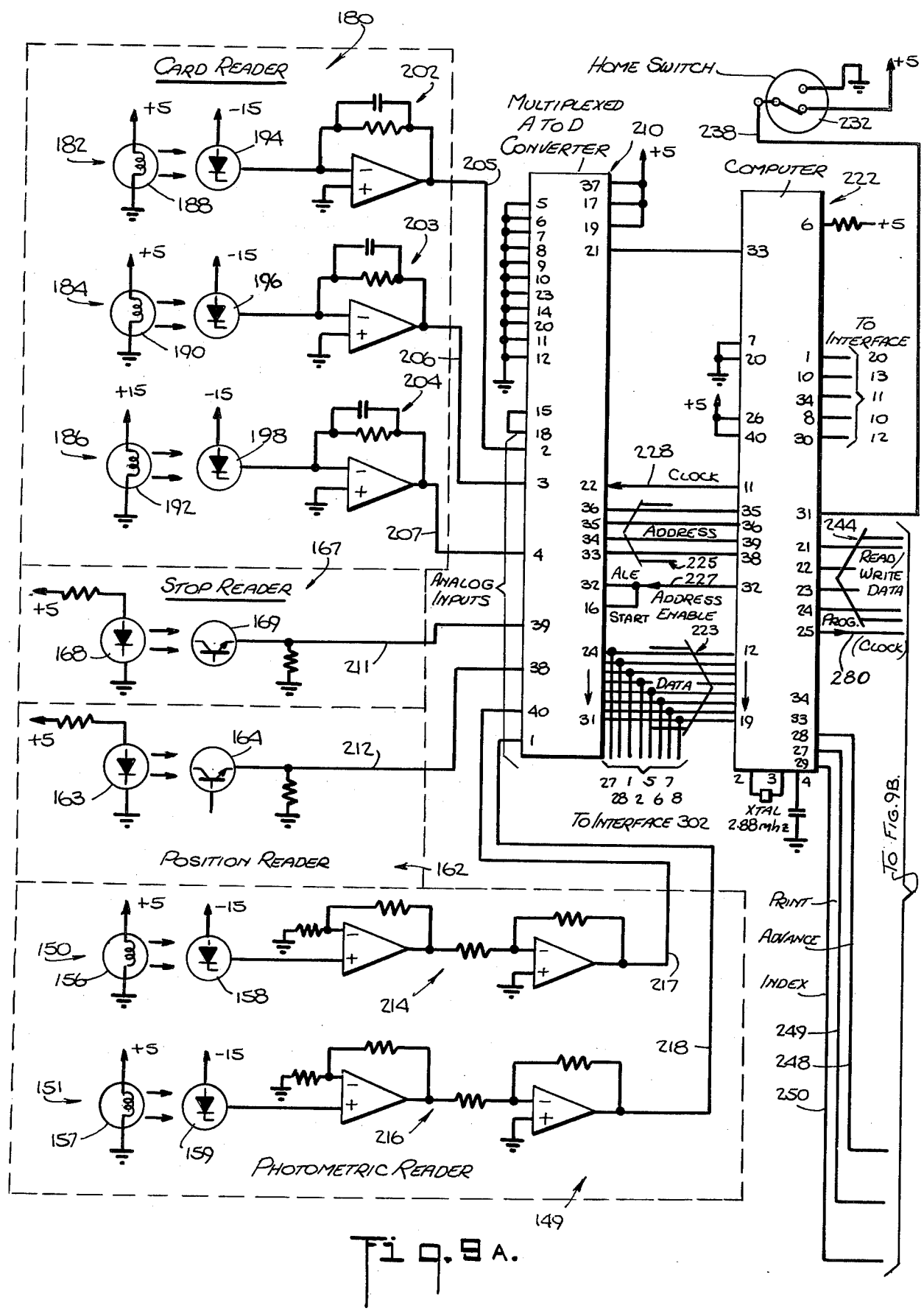

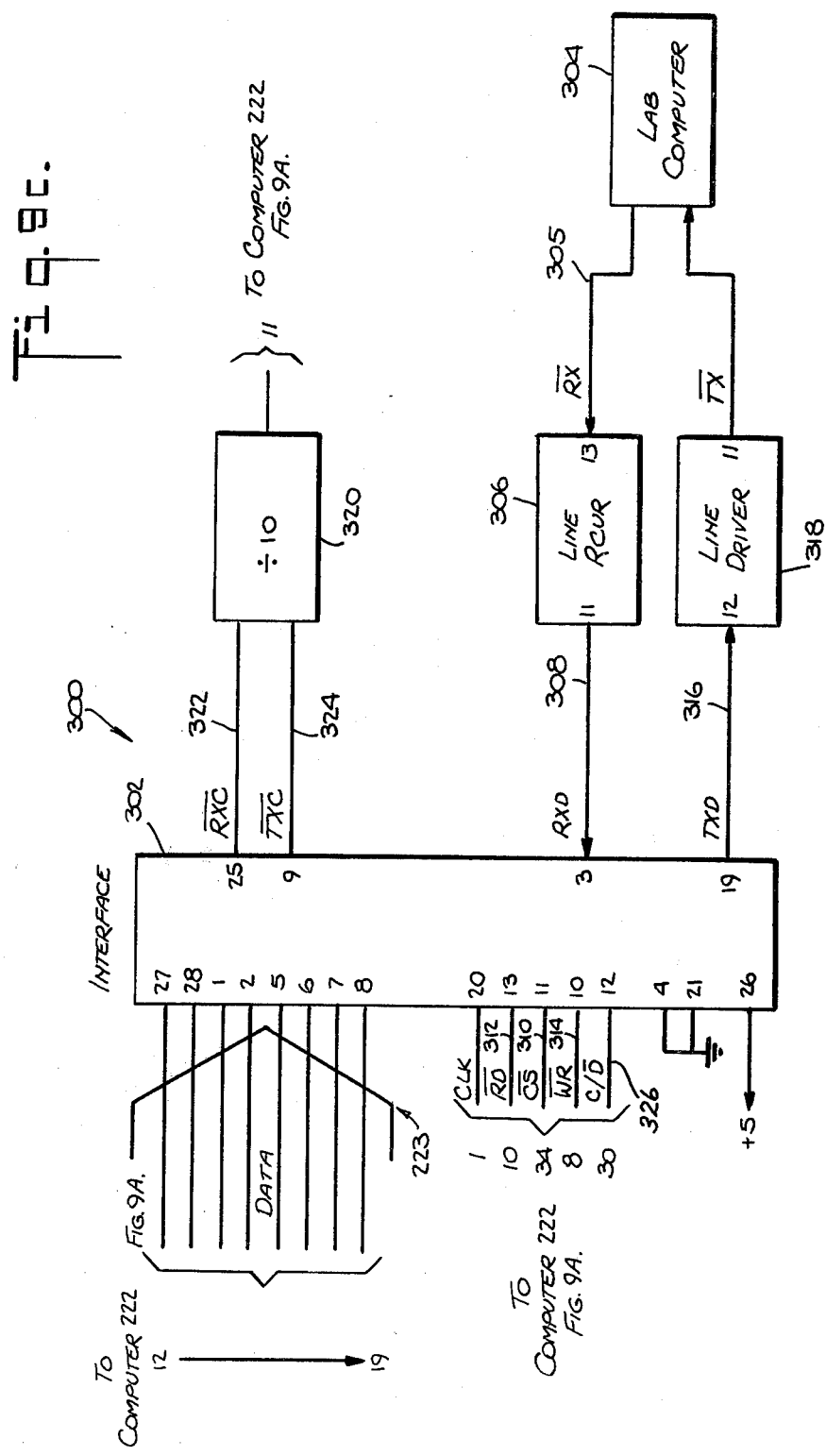

AUTOMATIC CHEMICAL ANALYSIS APPARATUS AND METHOD

BACKGROUND OF THE INVENTION

The present invention relates to a method and automatic apparatus for analyzing chemical samples and more particularly to a method and apparatus which automatically tests bacterial sensitivity to drugs.

DESCRIPTION OF THE PRIOR ART

U.S. Pat. No. 3,660,638 discloses card commanded automatic analyzing apparatus. The card contains information concerning the origin of the sample and command information regarding the analyses to be performed. The results of the analyses are entered on the card. U.S. Pat. No. 3,617,222 discloses another card commanded automatic analyzing apparatus in which the card contains origin information, command information and on which the analyses results may be entered.

Card commanded automatic analyzing apparatus are also disclosed in U.S. Pat. Nos. 3,775,595, 3,718,439, 3,680,967 and 3,917,455.

U.S. Pat. Nos. 3,928,140 and 3,832,532 disclose automatic bacterial sensitivity testers which are controlled by a central processing unit or computer.

U.S. Pat. No. 3,026,764 discloses an automatic bacterial sensitivity tester in which a plurality of test receptacles are passed stepwise through an observation or test station and test results are recorded on a record receiving member carried in a prearranged relationship with respect to each receptacle.

In U.S. Pat. Nos. 3,932,133 and 3,907,503, automated test systems are disclosed in which coded command information is read from the sample carrier and testing is carried out in accordance with this information.

U.S. Pat. No. 3,526,480 discloses an automated chemical analyzer which includes an analytical tape having information thereon for identifying the sample being analyzed and the test being run. The test results are entered on the analytical tape. A command tape controls testing.

It is, however, highly desirable that chemical samples be analyzed in variable analyzing sequences and that automated apparatus for analyzing chemical samples be capable of conducting tests in a variable analyzing sequence. In the specific case of testing bacterial sensitivity to drugs, it is desirable that a variable number of drugs and a variable number of concentrations of each drug be tested automatically. It is further desirable that the sequence of analysis be varied without the need to reprogram or readjust the apparatus.

SUMMARY OF THE INVENTION

It is an object of the present invention to provide a method for testing and/or identifying, i.e, analyzing, chemical samples automatically in variable analyzing sequences and a chemical analysis apparatus which is automatically operable in variable analyzing sequences.

It is also an object of the present invention to provide a method and apparatus in which variable analyzing sequences are automatically carried out without the need to reprogram or readjust the apparatus.

It is another object of the present invention to provide a method and aparatus for automatically testing bacterial sensitivity to drugs in variable testing sequences.

It is still another object of the present invention to provide a method and apparatus for automatically testing bacterial sensitivity to a variable number of drugs and/or a variable number of concentrations thereof.

It is a further object of the present invention to provide a photometric analysis method and apparatus for automatically, qualitatively and/or quantitatively testing bacterial sensitivity to a variable number of drugs and/or a variable number of concentrations of each drug without reprogramming or readjusting the apparatus.

It is still a further object of the present invention to provide a method and apparatus for automatically carrying out qualitative (Kirby-Bauer correlatable) tests on a sample of bacteria and a variable number of drugs and/or a variable number of concentrations of each drug.

These and other objects of the present invention are achieved in an apparatus and method in which the sequence of analyzing samples in a sample container is controlled by command means and in which the container is correlated with the command means. The command means and the sample container are matched so that for different matched sets of command means and sample containers, different sequences of analyzing may automatically be carried out without reprogramming or readjusting the apparatus.

An apparatus according to one aspect of the invention is provided for automatically testing and/or identifying, i.e. analyzing, a plurality of samples in a variable sequence by photometric measurements or electrical characteristics measurements (e.g. impedance measurements). The samples are contained in a plurality of adjacently disposed test cells or cupules in a sample container. Sequence information for the sequence of analyzing and for the recording of the analysis results is disposed on a source means and the analysis results are recorded on a record means. The apparatus comprises information sensing means for sensing command information of the analyzing sequence (sequence command information) from the source means and providing electrical signals representative of this information, sample characteristics determining means for providing additional electrical signals whose characteristics are determined by the nature of samples in the plurality of test cells, recording means for recording information representative of the photometric or electrical analysis (analysis information) of the samples on the record means, correlating means for correlating the source means, the information sensing means, the recording means and the record means, and computer circuit means for receiving the sequence command information signals and for receiving the photometric or electrical analysis signals, and in response thereto providing electrical signals for operating the correlating means and the recording means. More specifically, the computer circuit means receives the first signals corresponding to the sequence command information and second signals corresponding to the photometric or electrical analysis and provides signals to the correlating means which provides the proper correlation of the source means, the information sensing means, the recording means and the record means. The computer circuit means also provides signals to the recording means for recording the photometric or electrical analysis information. The computer circuit means includes memory means and is programmable to provide said signals in response to the first and second signals, the memory and the program.

In accordance with an aspect of the invention, the sequence command information is disposed on a source/record means on which the photometrical or electrical analysis information is recorded.

In the preferred embodiment of the invention, the samples are analyzed photometrically and a source/record means is provided. Thus, apparatus according to the preferred embodiment of the invention includes photometric means for photometrically analyzing the samples. The correlating means comprises cell indexing means for providing relative movement between the photometric means the cells. Further in accordance with the preferred embodiment, the correlating means also includes additional indexing means for providing relative movement between the source/record means and the information sensing means and between the source/record means and the recording means. The computer circuit means in response to the first and second signals provides third signals to the cell indexing means, fourth signals to the additional indexing means and fifth signals to the recording means for recording the photometric analysis information.

The apparatus according to the preferred embodiment further comprises photoelectric means for determining the position of the cells relative to the photometric means. The apparatus also comprises additional photoelectric means for determining the location of a predetermined cell relative to the photometric means. The additional photoelectric means are used to determine the occurrence of an end of test condition in which the sample container has been indexed through a complete cycle. Signals from the position and end of test photoelectric means are provided to the computer circuit means.

The method and apparatus according to one aspect of the invention are capable of automatically testing bacterial sensitivity to a variable number of reagents (for example drugs) and/or a variable number of concentrations of each reagent. Thus, sample containers are provided in which the number of reagents and/or the number of concentrations of each reagent vary from container type to container type and corresponding command means are provided for each type of sample container which differ in the number of reagents and/or concentration of each reagents that are to be tested.

In accordance with a preferred embodiment of the invention, sequence command information is recorded on the source/record means and the sequence command information is sensed from the source/record means. The source/record means is also provided with space to record the results of the testing, an identification of the reagents tested, and identification of the bacteria specimen and its source. The reagent information and the recording of the test results are correlated so that the source/record means will bear the recorded result of the testing of each reagent, i.e., whether the bacteria grew or did not grow in each concentration of each reagent.

The sample container is positioned relative to the photometric means so that the samples in the cupules or cells are photometrically analyzed in the desired sequence. In the preferred embodiment, the sample container is a carousel-type container having a multiplicity of cupules or cells for holding individual reagents arranged about the periphery of the container. A predetermined amount of a bacterial suspension is introduced into each cupule to produce test reaction mixtures (hereinafter mixtures). The carousel-type container is then indexed by the cell indexing means to permit testing of the mixtures.

The source/record means includes a surface having the sequence command information recorded thereon and spaces for recording the photometric analysis information for each mixture thereon. The source/record means surface also has recorded thereon the identification of each mixture to be analyzed adjacent to which space is provided for recording the photometric analysis information. Additionally, reagent information is provided on the source/record means adjacent to which the sequence command information for each mixture is located so that the reagent identification, the sequence command information for that mixture, and the space for recording the photometric analysis information for that mixture extend along a common line.

According to the preferred embodiment of the invention, the apparatus and method are adapted to analyze photometrically the effect of drugs on bacterial growth and carry out qualitative (Kirby-Bauer correlatable) or quantitative dilution tests. In such tests, the samples of bacterial are standardized to have a known bacteria count per ml of liquid. In a quantitative dilution test, the lowest drug concentration which allows no visible growth of bacteria, the Minimum Inhibitory Concentration (MIC), may be determined from the test results of all the concentrations of the drug. The effectiveness and necessary dosage of a drug depends upon the test results for all concentrations thereof. In a qualitative test, standardized samples of a bacteria are tested for sensitivity to a drug. After incubation, each concentration of the drug is individually tested for its effect.

For example, in testing two concentrations of a drug, if the bacteria are killed or their growth prevented in both concentrations of the drug, then the bacteria is "Sensitive" (S) to the drug in the tested concentrations. If the bacteria grow in both concentrations of the drug, then the bacteria are insensitive or "Resistive" (R) to the drug in the tested concentrations. If the bacteria grow in the lower concentration but not in the higher concentration, the bacteria is in an "Intermediate" (I) classification with respect to the drug and the MIC is the higher tested drug concentration; and if the bacteria do not grow in the lower concentration but do grow in the higher concentration, the test is termed "Nonsense" (N). Table 1 below summarizes a qualitative test for two drug concentrations with "+" indicating bacteria growth for a particular concentration and "−" indicating that there has been no growth for a particular concentration.

TABLE 1

| Low Conc. | High Conc. | Effectiveness |
|---|---|---|
| − | − | S |
| + | − | I |
| + | + | R |
| − | + | N |

In accordance with a preferred embodiment of the invention, to carry out such testing, each of the cells is charged with a given standardized bacteria sample and a drug. Different cells contain the same given standardized bacteria sample and different drugs or different concentrations of the same drug. The sequence command information correlates the different drugs with the test cells and the different concentrations of the same drug with the test cells. Thus, the sequence command information indicates the particular sequence to be carried out, i.e. whether a single concentration of a drug is to be analyzed or whether two or more concentrations of the same drug are to be analyzed. The computer circuit means receives this sequence command information and provides control signals for the correct indexing of the sample container correlated with the recording of the photometric analysis information.

In the preferred embodiment, the source/record means comprises a card, ticket or sheet which includes sequence command information for analyzing a plurality of cells containing the same standardized bacteria sample and different drugs in different concentrations. The computer circuit means correlates the third, fourth and fifth signals to the cell indexing means, the additional indexing means and the recording means, respectively, so that recording of the photometric analysis information is correlated to the correct drug and the correct concentration thereof.

The computer circuit means is operative to receive and process the photometric signals for the different concentrations of the same drug, compare the photometric signals for each concentration to a reference value, and provide sixth signals indicative of whether bacterial growth in all of the different concentrations of the same drug are greater than the reference value or not. The computer circuit means is further operative to provide said sixth signals which are indicative of whether some of the different concentrations of the same sample are greater than the reference value and some are less than the reference value.

The photometric means in the preferred embodiment comprises a plurality of light emitters and corresponding light detectors in order that the contents of a number of cells up to the number of emitters and detectors may be simultaneously analyzed. The recording means in the preferred embodiment comprises a decade printer including a number of decades equal to the maximum number of concentrations of a drug to be analyzed, a different decade being assigned for printing the photometric analysis information for each concentration or the interpretive results. In the illustrated embodiment, a maximum of three concentrations of any drug are tested and the decade printer comprises three adjacently disposed decades and said source/record means comprises a sheet having three linearly, juxtaposed spaces adjacent to the identification of each of a plurality of drugs, a respective space being provided for recording the photometric analysis information of a respective concentration of the drug.

Further, in accordance with the preferred embodiment, the drug identification, the spaces for the different concentrations thereof and the sequence command information for each drug are linearly juxtaposed on the sheet. The sequence command information on the sheet indicates the number of concentrations to be tested and the order of testing and printing of the results thereof. The cell indexing means includes a motor for indexing the container past the photometric means. The additional indexing means comprises pressure roller means for engaging the source/record sheet and advancing it past the information sensing means and the decade printer, and the information sensing means comprises photoelectric means operative to sense an optical sequence code disposed on the sheet adjacent to the drug identification.

These and other aspects of the invention will be more apparent from the following description of the preferred embodiment when considered with the accompanying drawings.

BRIEF DESCRIPTION OF THE DRAWINGS

The present invention is illustrated by way of example and not limitation in the figures of the accompanying drawings in which like numerals indicate similar parts and in whch:

FIG. 5 is another sectional view of the receptacle of FIG. 3.

FIG. 8 is an illustration of the source/record sheet of the apparatus of FIG. 2; and FIGS. 9A–9C are a composite schematic circuit and block diagram of the apparatus of FIG. 2.

DESCRIPTION OF THE PREFERRED EMBODIMENT

Figure 1:
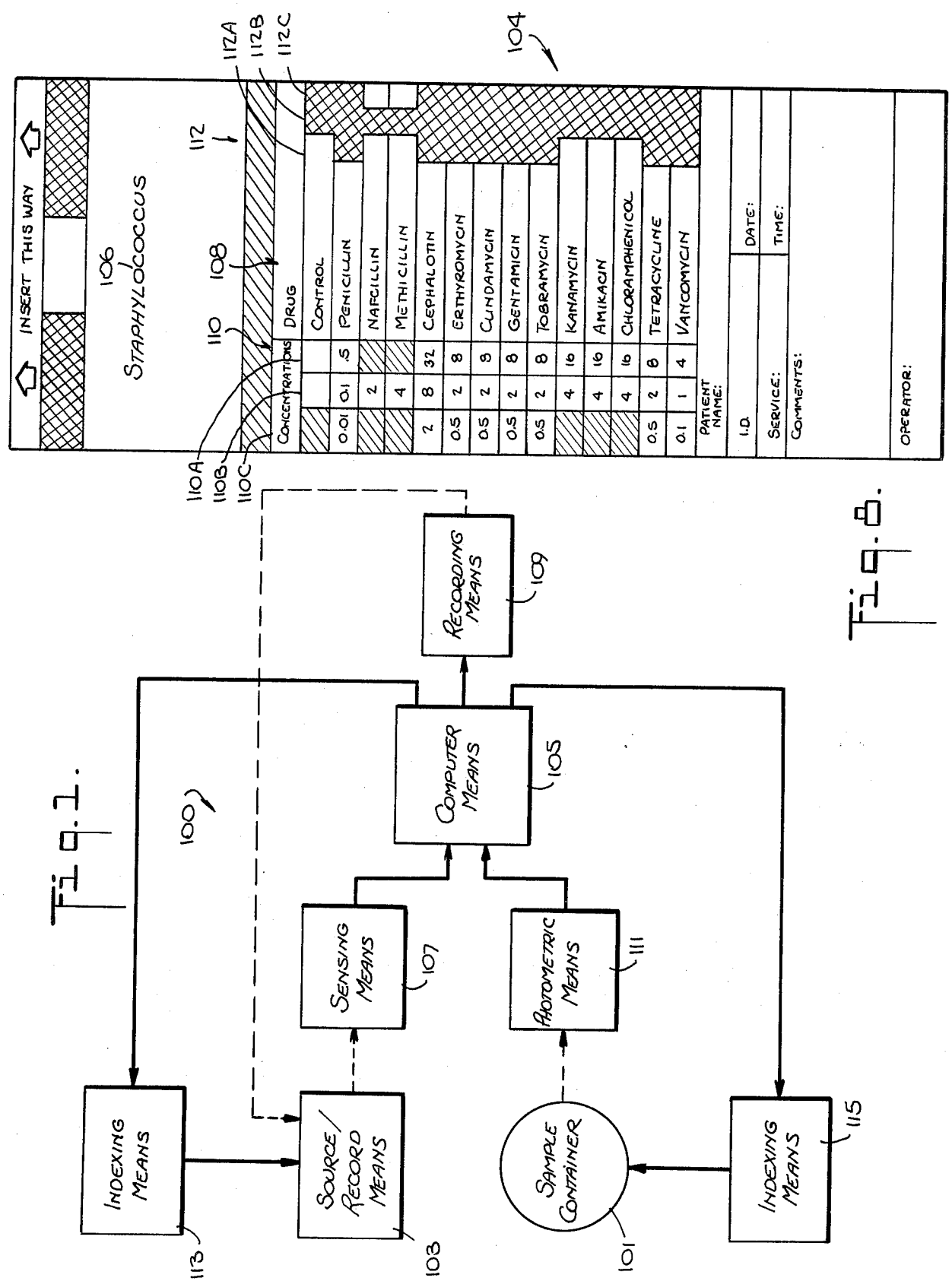
FIG. 1 is a block diagram of the apparatus according to the invention.

Referring now more particularly to the drawings, the system 100 shown in block form in FIG. 1 tests the resistance (susceptance) of bacteria contained in test cells of a container 101 to different drugs under command of a source/record means 103. The source/record means 103 provides command information to the system computer means 105 via the sensing means 107 to control the sequence of the testing, and the sequence of recording the test results thereof on the source/record means 103 by recording means 109. The source/record means 103 bears identification of the bacteria, the drugs being tested and the concentrations of each drug being tested. Source/record means 103 and sample containers 101 are correlated so that containers having varying numbers of drugs in varying concentrations may be automatically tested in varying sequences in accordance with the appropriate source/record means. The computer means 105 receives the command information from the source/record means 103 and provides for the photometric testing of the sample in the container 101 by the photometric means 111. The test information is fed to computer means 105. In response to the command information, the computer means provides for indexing of the source/record means 103 and the container 101 by indexing means 113, 115 respectively. The computer also controls the recording means 109 in response to the command information for recording the results of the photometric tests on the source/record means 103 in accordance with the test information from the photometric means 111.

Figure 6:
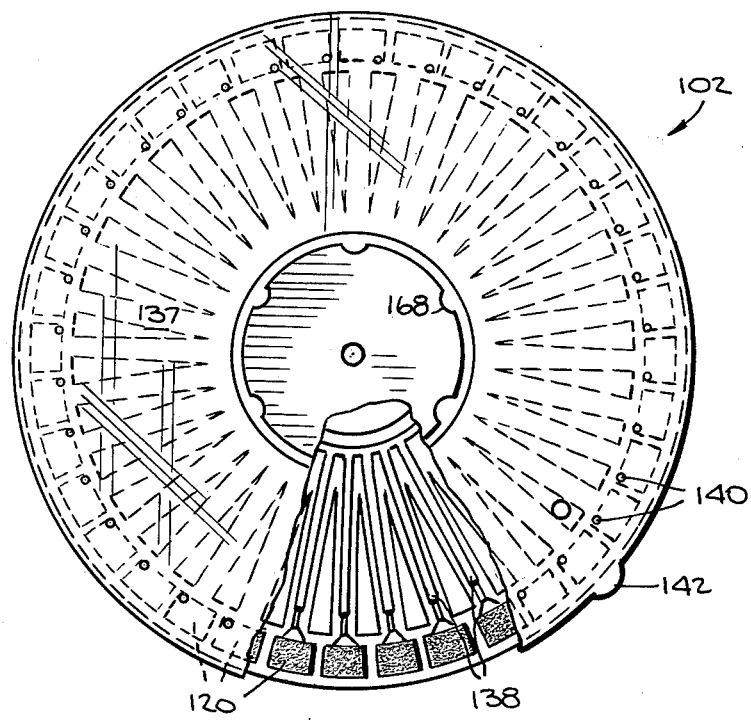
FIG. 6 is a top plan view of the carousel container of the apparatus according to the invention.

More specifically, the system 100 (FIGS. 2–5 and 9) tests the resistance (susceptance) of bacteria contained in test cells of a container 102 (FIGS. 6 and 7) to different drugs under command of a card 104 (FIG. 8). The card 104 provides command information to the system to control the sequence of the testing, and the sequence of printing of the test results thereof on the card. The card bears identification of a group of bacteria 106, the drugs 108 being tested and the concentrations 110 of each drug being tested. The card 104 also has encoded thereon the system command information 112. Cards and sample containers are correlated so that containers having varying numbers of drugs in varying concentrations may be automatically tested in varying sequences in accordance with the appropriate card. Thus, it is not necessary to reprogram or readjust the apparatus to vary the testing sequence for containers having different numbers and concentrations of drugs.

Card 104 shown in FIG. 8 includes the command information for one of the testing sequences. The drugs are listed in a centrally located column with the concentrations of each of the drugs to be tested indicated to the left of the respective drug in columns along the left side of the card. The system command information 112 for each drug is encoded to the right of the respective drug in columns along the right side of the card corresponding to the concentrations in the columns along the left side of the card. In the card illustrated in FIG. 8, there is space for indicating up to three concentrations for each drug. Thus, the spaces for the concentrations are arranged in three columns 110A, 110B and 110C along the left side of the card. Correspondingly, three spaces are provided to the right of each drug for encoding command information for that drug with the spaces also being arranged in three columns 112A, 112B and 112C along the right side of the card. The command information indicates whether one, two or three concentrations of a particular drug are to be tested. The test result for each concentration of each drug is printed over the indicated concentration to the left of the respective drug. The system illustrated in FIG. 1 prints the symbols "+" and "−" (not shown) over the concentration to indicate the nature of the test results.

Figure 2:
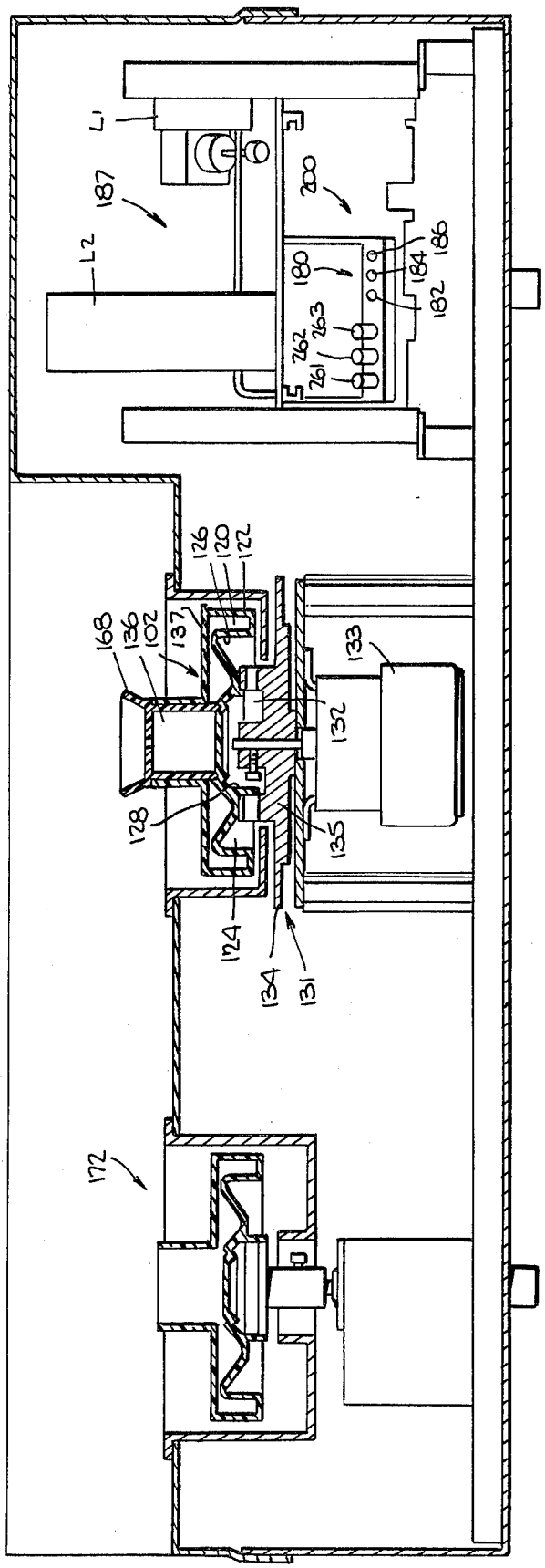
FIG. 2 is an elevation view of the apparatus according to the invention.
Figure 3:
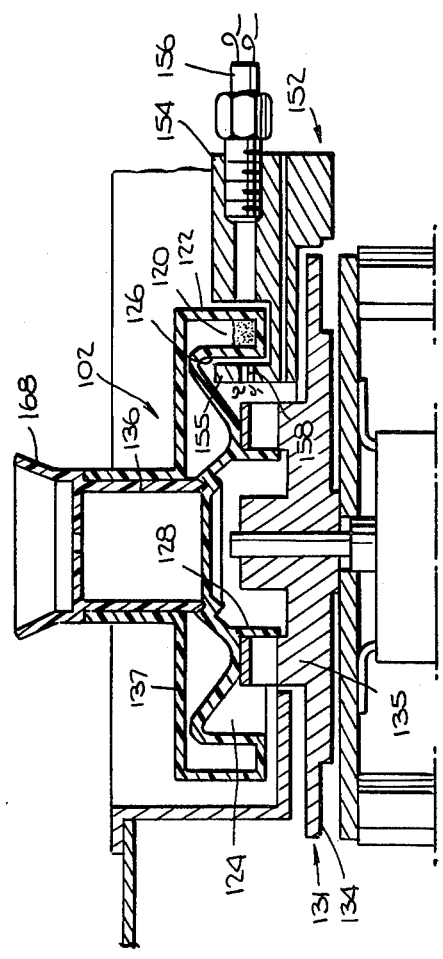
FIG. 3 is an enlarged plan view of a portion of the apparatus of FIG. 2 depicting the carousel container receptacle and printer.
Figure 3:
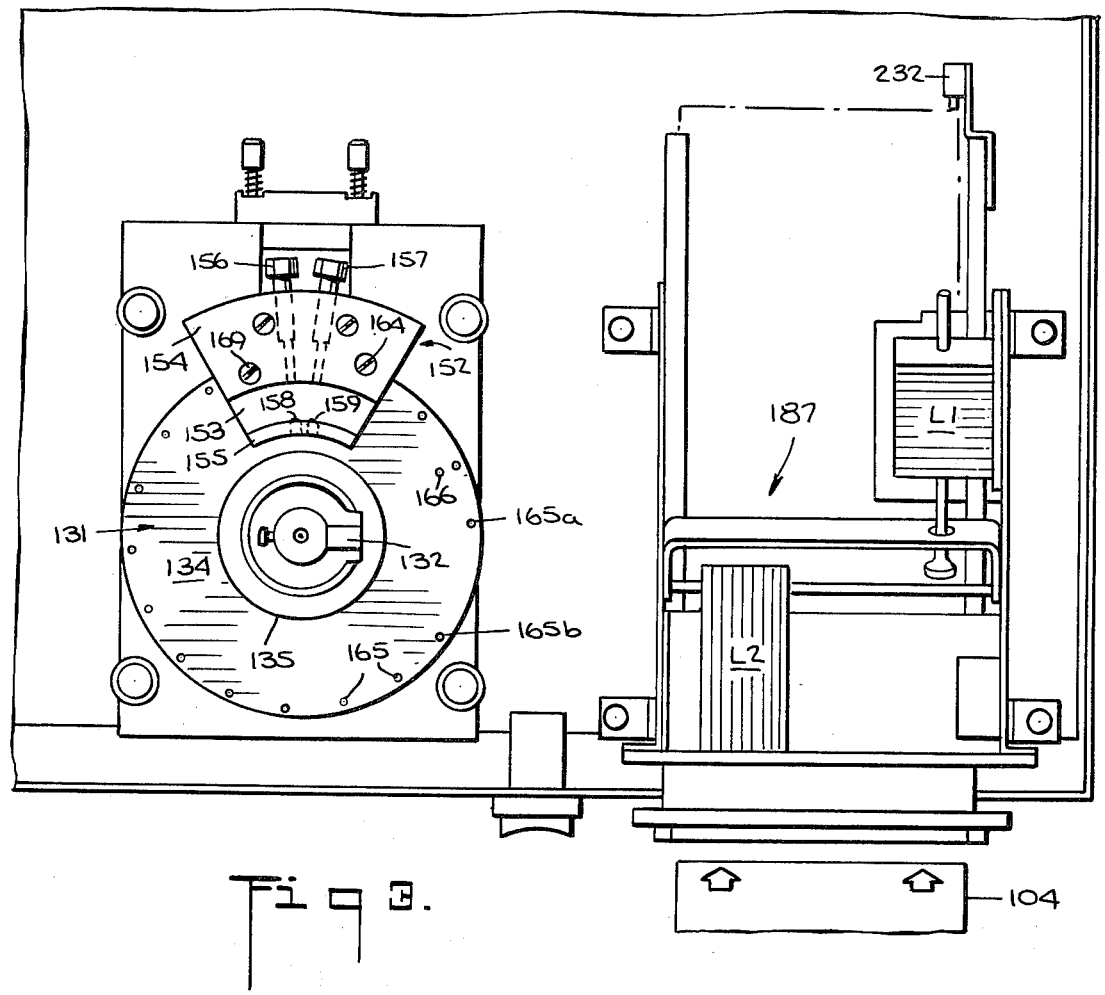
Figure 4:
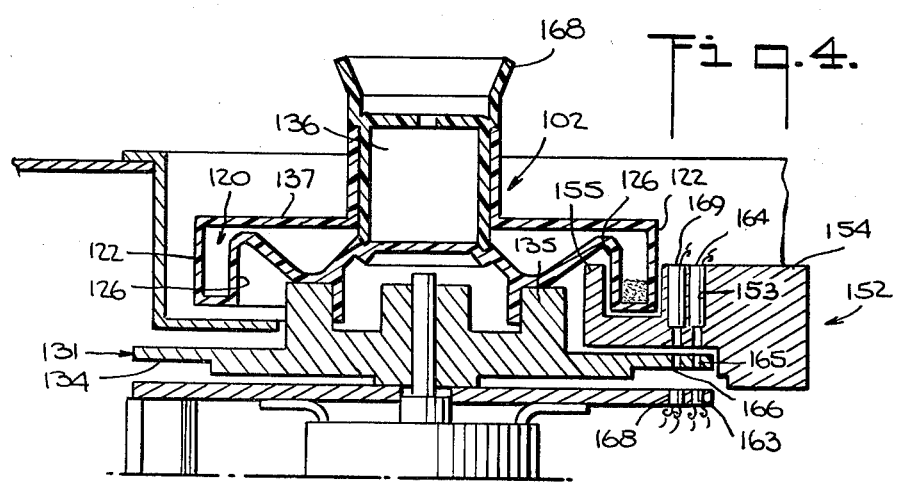
FIG. 4 is a schematic sectional view of the receptacle of FIG. 3.
Figure 7:
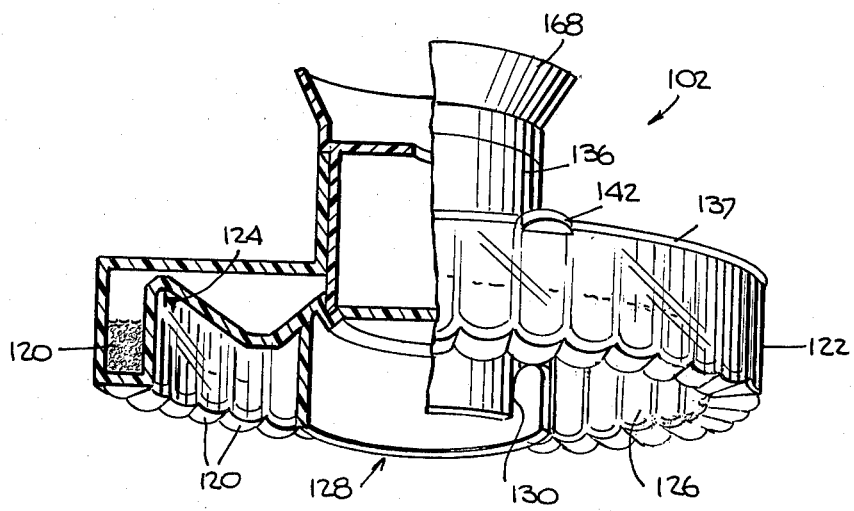
FIG. 7 is a bottom perspective view of the carousel container shown in FIG. 6.

The containers 102 (FIGS. 6 and 7) is of the carousel type and includes thirty-six cupules or test cells 120 arranged about the periphery of the container. The container 102 has the general shape of a disc with the outer peripheral walls 122 of the cupules defining the exterior periphery of the container. A annular cavity 124 in the bottom of the container (FIG. 7) exposes the interior walls 126 of the cupules 120. The cavity 124 extends from the interior walls 126 of the cupules to a centrally located circular key 128. A keyway 130 in the key 128 is received in a receptacle 131 in the apparatus and engaged by an indexing arm 132 driven by an indexing motor 133 (FIGS. 2, 3 and 7). The receptacle 131 includes a discshaped base member 134 and a central container-engaging portion 135. The container key 128 is received in the receptacle central portion 135 with the indexing arm 132 engaging the keyway 130 of the container. The receptacle central portion 135 and the base member 134 are secured together and both are rotated by motor 133. Thus, the carousel container 102 is rotatably engaged in the receptacle 131 in the system 100 under control of motor 133 so that the carousel container may be rotatably indexed upon energization of motor 133. The container 102 includes a central feed cylinder 136 in the top 137 of the container which is communicated with each of the cupules 120 by identical radially-extending passages 138 from the central feed cylinder 136 to the cupules 120. Small apertures 140 in the top 137 of the container communicate the interior of each of the cupules with the atmosphere. A locater tab 142 is provided in the top of the container in radical registration with the keyway 130 of the key 128. The tab facilitates alignment of the keyway 130 with the indexing arm 132.

The contents (test reaction mixtures) of each of the cupules 120 are analyzed photometrically. A photometric reader 149 (FIG. 9A) detects light transmitted through the cupules by means of a pair of photometric test readers 150, 151 (FIGS. 3 and 5). Each test reader 150, 151 is disposed approximately in a wedge-shaped optical assembly 152 above the receptacle 131. The assembly 152 is located radially outwardly of the receptacle central portion 135 and radially extends beyond the periphery of the receptacle base member 134. Assembly 152 includes an annular recess 153 therein and outer 154 and inner 155 peripheral regions. Two circumferentially spaced lamps 156, 157 are disposed in the outer peripheral region 154 and extend radially inwardly towards the inner peripheral region 155. Two circumferentially spaced diode detectors 158, 159 are disposed in the inner peripheral region 155 and are radially optically aligned with lamps 156, 157, respectively. The annular recess 153 is sized to receive the cupules 120 of the container 102 therein. The lamps 156, 157 extend in the outer peripheral region 154 to adjacent the recess and correspondingly to adjacent the exterior wall 122 of the cupules when the container 102 is mounted in the receptacle 131. The diode detectors 158, 159 are disposed in the inner peripheral region 155 of the assembly adjacent to the recess 153 and correspondingly adjacent to the interior wall 126 of the cupules when the container is mounted in the receptacle 131. Each pair of lamps and diode detectors 154, 158 and 155, 159, respectively, is disposed along a generally radial optical axis so that the light emitted by the lamps 154, 155 will pass through a respective cupule and will be detected by the respective diode detector 158, 159. Rotation of the container 102 indexes the cupules through assembly 152 in the recess 153 thereof past the lamps and aligned diode detectors.

A position reader 162 (FIG. 9A) is used to determine the position of each cupule relative to the readers 150, 151. Position reader 162 comprises a light-emitting diode (LED) 163 and a phototransistor 164 which are optically disposed (FIGS. 3 and 4) generally vertically with respect to base member 134. The base member 134 of receptacle 131 includes a series of holes 165 circumferentially spaced about the periphery thereof. Seventeen holes 165 are provided with equal spacing between the holes except for the last two holes 165a, b. The spacing between holes 165a, b is twice that between the other holes. The LED and phototransistor of the position reader 162 are disposed along a generally vertical optical axis which vertically intersects the peripherally-extending location of the series of holes in the base member 134. LED 163 is disposed below the base member 134 in the frame of the apparatus and phototransistor 164 is disposed above the base member in the assembly 152. The LED 163 extends upwardly to adjacent the bottom of the base member 134 and the phototransistor 164 extends downwardly from assembly 152 to adjacent to top of base member 134. The photo-transistor 164 detects the light from the LED 163 each time a hole 165 passes between the LED and the phototransistor. The holes 165 correspond to the positioning of a pair of cupules 120 with respect to the readers 150, 151. The container 102 is rotated and system timing obtained with respect to adjacent holes 165. Thus, a pair of cupules 120 is indexed past the readers and the photometric analysis conducted in accordance with the detection of adjacent holes 165. The container may be stopped each time a hole 165 is detected and the photometric analysis conducted or the container may be continually rotated with detection of the holes providing timing for conducting the photometric analysis.

As mentioned above, the spacing between holes 165a, b is twice that between the other holes. This spacing corresponds to permitting the last two cupules which are reserved for control purposes to pass the reader 149 without photometric analysis.

Figure 9B:
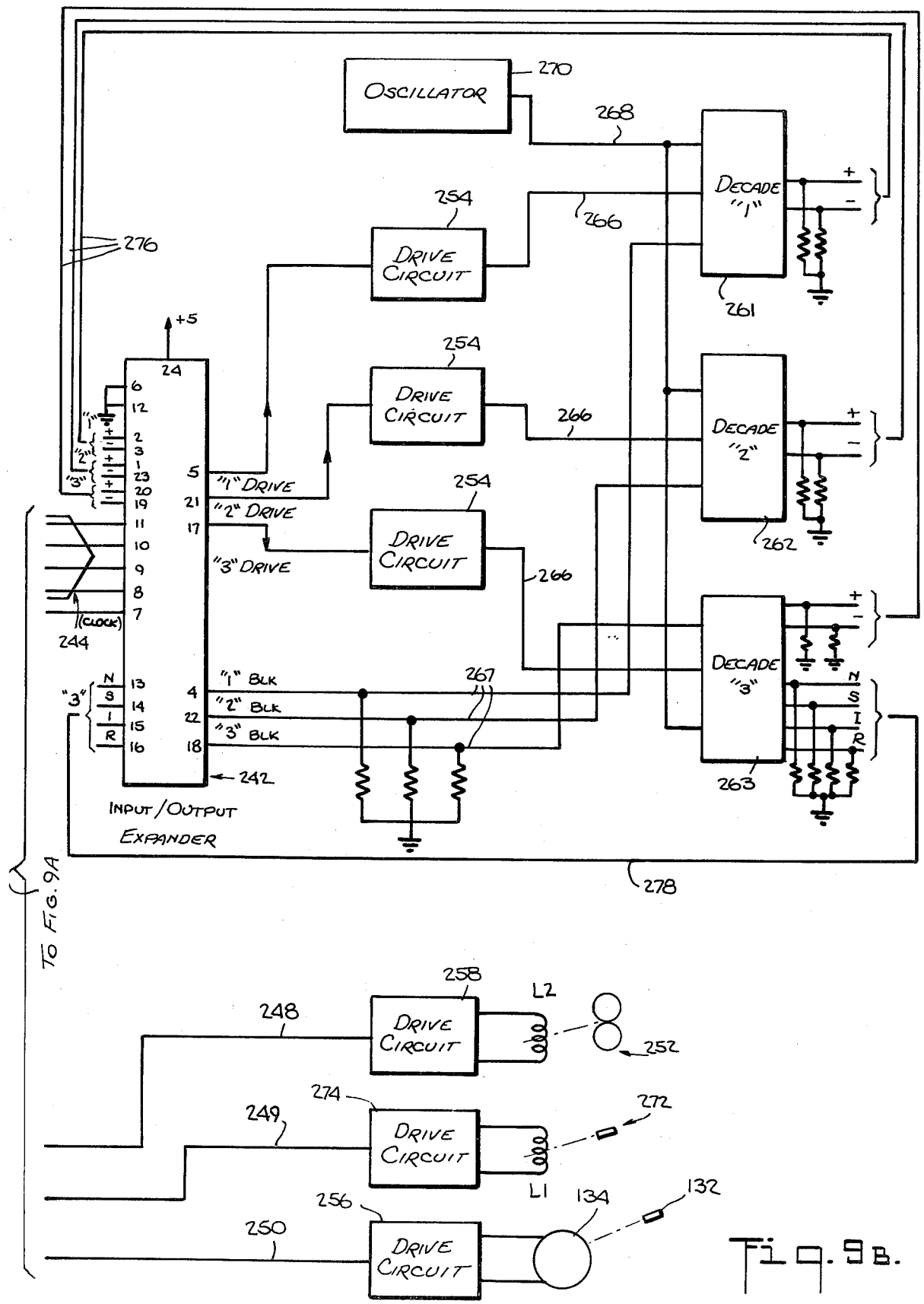

The base member 134 also includes a single hole 166 located radially inwardly of holes 165. This hole is detected by a stop reader 167 (FIG. 9A). The stop reader 167 is identical to the position reader and includes an LED 168 (FIGS. 3 and 4) and a photo-transistor 169. The LED 168 is disposed in the apparatus below the base member 134 similarly to LED 163 and radially inwardly of LED 163 with respect to the base member 134. The phototransistor 169 is disposed in assembly 152 above the base member 134 similar to phototransistor 164 and radially inwardly of phototransistor 164 with respect to the base member 134. The LED 168 and phototransistor 169 are vertically optically aligned and positioned to be radially aligned with hole 166. The stop reader 167 detects the presence of hole 166 between the LED 168 and phototransistor 169 similar to the manner in which the position reader 162 detects the presence of holes 165. Detection of hole 166 indicates a complete 360° rotation of the container for terminating a test or commencing a test.

As will be discussed more fully hereinafter, the container 102 is adapted to be indexed to move the cupules 120 past the test readers 150 and 151 so that the contents of the cupules may be photometrically analyzed. The stop reader 167 acts to detect the hole 166 to terminate the test when the container has progressed through a complete 360° index. The position reader 162 acts to detect holes 165 so that a photometric test is conducted when a respective cupule is in registration with the radial axis of a respective test reader 150, 151.

The cupules 120 of the carousel container 102 are filled with a variety of drugs each with one or more different strengths or concentrations. As mentioned, there are thirty-six cupules in the carousel container 102. Four of the cupules are provided as references and for control purposes and accordingly contain only the bacteria sample and no drugs. The remaining cupules contain a designated drug in a designated concentration, and the standardized bacteria sample in a nutrient, i.e., a test reaction mixture. The first two and last two cupules, designated as cupules "1" and "2", and as "35" and "36", respectively, are reserved as the reference and control cupules with cupule "1" being adjacent the tab 142. Cupules "3" through "34" will contain the mixture of the bacteria sample, nutrient and a drug.

Referring to the card 104 in FIG. 8, the undarkened spaces to the left of "Control" and to the left of the designated drugs correspond to a numbered cupule while the darkened spaces do not correspond to any cupule. The spaces in columns 110C and 110B to the left of "Control" correspond to cupules 1 and 2. The spaces in columns 110A, 110B and 110C to the left of "Penicillin" for concentrations of "0.01," "0.1" and "0.5," respectively, correspond to cupules 3, 4 and 5, respectively. The space in column 110B to the left of "Nafcillin" for a concentration of "2" of Nafcillin corresponds to cupule 6 and the space in column 110B to the left of "Methicillin" for a concentration of "4" corresponds to cupule 7. In similar fashion, the spaces to the left of the other drugs correspond to the other cupules with the space in column 110C to the left of "Vancomycin" for a concentration of "4" for Vancomycin corresponding to cupule 34. Cupules 35 and 36 are reserved for control purposes and there is no correspondence for these two cupules to a location on card 104.

One sample of cultured bacteria in a standardized concentration is prepared. The container 102 is provided with the designated drug therein in the respective cupule in accordance with the sequence set forth on card 104. The bacteria sample is introduced into the container 102 through the central feed cylinder 136. A predetermined quantity of the bacteria sample in the standardized concentration sufficient to provide a predetermined equal amount of sample to each of the cupules is discharged into the central feed cylinder 136 and a cap 168 is placed in the feed cylinder to close it off and prevent loss of sample therefrom. The container 102 is then placed in the spinning receptacle 172 provided in the apparatus (FIG. 2) and rotated to distribute the sample radially outwardly from the central feed cylinder to the cupules through passages 138 by centrifugal force, the cupules being vented by apertures 140. After the bacteria sample has been disributed into the cupules to provide the test reaction mixtures therein, the container is placed in an appropriate environment to further culture or incubate the bacteria. Thereafter, the effect of the drugs on the bacteria is ready to be tested by system 100.

As mentioned, the card 104 provides command information to the system 100 for controlling the sequence of testing and printing. The command information is contained in columns 112A, 112B and 112C located along the right side of the card to the right of the "Control" and the drug identification. The darkened spaces to the right of the drugs correspond to concentrations of the drug on the left, i.e., a darkened space to the right of "Control" and the drugs corresponds to an undarkened space to the left thereof and vice-versa. A darkened space to the right of a drug in a respective column indicates that a test is to be performed for the cupule corresponding to that drug. For example, the darkened spaces in columns 112B and 112C to the right of the "Control" indicates that a control reading is to be taken for cupules 1 and 2. Similarly, the darkened spaces in columns 112A, 112B and 112C to the right of "Penicillin" indicate that tests are to be run on cupules 3–5 for the different concentrations of Penicillin. For Nafcillin, only the central space in column 112B is darkened corresponding to the test to be run for the single cupule 6 containing Nafcillin.

Referring now to FIGS. 2, 3 and 9A, the sequence information 112 is entered into the system 100 by means of the card reader 180. The card reader comprises three readers 182, 184 and 186 arranged in a side-by-side relationship in correspondence with columns 112A, 112B and 112C. The card reader 180 is located at a read/print station 187 in the apparatus so that the card 104 may be read by the card reader 180 and the results of photometric analysis may be printed thereon without the need to transfer the card to another location. Printing is accomplished by a decade printer 200 which will be described hereinafter. Infrared lamps 188, 190 and 192 of the card reader 180 emit infrared light towards columns 112A, 112B and 112C, respectively. The diode detectors 194, 196 and 198 are disposed to detect the infrared light reflected from columns 112A, 112B and 112C, respectively. The darkened spaces will absorb the infrared light emitted by lamps 188, 190 and 192 while the undarkened spaces will reflect the emitted light.

The presence or absence of a darkened space in a column is detected by a respective reader and converted to electrical signals which are amplified by respective amplifiers 202, 203 and 204 and supplied as analog inputs on lines 205, 206 and 207, respectively, to the multiplexed analog to digital (A to D) converter 210. The cupule position information and the end of test (stop) information are also converted to electrical signals by readers 162 and 167, respectively, and supplied as analog inputs on lines 211 and 212, respectively, to the A to D converter 210.

Test readers 150 and 151 provide turbidimetric analysis of the contents of each cupule. As is known in the art, the presence of bacteria in a liquid mixture will act to attenuate light projected into the mixture. If the bacteria can multiply in the presence of the given drug concentration in a given cupule, the increased concentration of bacteria transmits less light directly through the liquid mixture, than would the initial standardized concentration. Thus, the lower the level of light detected by diode detectors 158 and 159, the higher the concentration of bacteria in the mixture, i.e., the effectiveness of a given drug concentration is inversely proportional to the bacteria concentration in the cupule. The light detected by diode detectors 158 and 159 is converted into electrical signals which are amplified by amplifiers 214 and 216, respectively, and supplied as analog inputs on lines 217 and 218, respectively, to the A and D converter 210 in proportion to the amounts of light detected by the detectors 158 and 159.

The information supplied to the A to D converter 210 on lines 205-207 from card reader 180, on lines 211 and 212 from the position and stop readers 162, 167, respectively, and from the photometric reader 149 on lines 217, 218 are converted to digital signals and fed to computer 222 on an eight bit data line 223. The analog inputs 205, 206, 207, 211, 212, 217 and 218 are multiplexed for conversion of the analog values thereon to a corresponding eight bit digital signal under control of a four bit digital address signal which is supplied to the A to D converter 210 on line 225 from computer 222. An eight bit digital signal representative of an analog value at a multiplexed analog input is thus supplied to the computer upon the computer supplying the appropriate digital address signal to the A to D converter. The A to D converter 210 is also provided with an address enable on line 227 and a clock signal on line 228 from computer 222.

In addition to providing the address for multiplexing the A to D converter 210 and receiving digital data in response thereto, the computer 222 also receives information as to the position of card 104 in card reader 180 at the read/ print station from "Home" switch 232 on line 238. "Home" switch 232 is a microswitch disposed in the card reader at a "Home" location so that the switch is activated by the end of the card 104 when it is fully inserted or "Home" in the card reader. The card reader 180 continually transmits information to the computer 220 via the A to D converter 210 when the apparatus is on. When a card is inserted and a particular code encountered (e.g. 000), the presence of the card in the reader is detected.

Still further digital information, which relates to the decade printer 200, is supplied to computer 222 by an input/output (I/O) expander 242 on a four bit read/write data line 244. The read/write data line interconnections between computer 222 and I/O expander 242 are also used to provide a four bit data output from the computer to the I/O expander. Thus, the four lines 244a-244d form a four bit bi-directional port for the computer and the I/O expander. The computer provides outputs directly to the printer on lines 248-250 to control printing in conjunction with the I/O expander as will be described hereinafter.

The computer 222 is programmed in assembly language to receive the information on data line 223, read/write data line 244, and switch line 238, and provide commands which ultimately control operation of the decade printer 200, the pressure roller advance 252 for indexing the card 104 and the indexing motor 133 for indexing the container 102 in addition to providing the address and the clock and enable signals to the A to D converter. The decade printer 200, the drive circuits 254 therefor, the indexing motor 133 and its drive circuit 256, and the pressure advance roller 252 and its drive circuit 258 are conventional and, therefore, will not be described in detail.

Decade printer 200 comprises three decades, decades 261-263, which are arranged in juxtaposition at the read/print station 187 and adapted to print along columns 110A, 110B, 110C, respectively, on card 104. Each of decades 261-263 includes indicia which indicate the results of the turbidimetric analysis. In system 100, the symbol "+" is used to indicate that bacteria has grown in the presence of a drug while the symbol "−" is used to indicate that the bacteria have not grown or have been killed. Additionally, each of the decades 261-263 may be blanked so that no information will be printed, if desired. Upon command of computer 222, each of the decades 261-263 is rotated by a drive signal 266 (or blanked by a blanking signal 267) in conjunction with a timing signal 268 from oscillator 270 to position the decade in the printing position. A drive signal from a respective drive circuit 254 on a corresponding line 266 under control of computer 222 causes positioning of the decade for printing the selected indicia or a blanking signal on lines 267 causes the decade to be blanked. Thus, in accordance with information from card reader 180 and photometric analyzer 149, the appropriate indicia, i.e., a "+", a "−" is selected for each of decades 261-263, or the decade may be blanked. Actual printing is accomplished by the strike of hammer 272 against decades 261-263 upon energization of solenoid L1 by computer 222 through drive circuit 274. After each printing, pressure roller 252 is energized by solenoid L2 under control of computer 222 through drive circuit 258 to advance the card 104 so that the spaces in columns 112A, 112B and 112C for a particular drug are read by reader 180, and the spaces 110A, 110B and 110C for the same drug are in registration with the decades 261-263 for the strike of hammer 272.

The command information for controlling the strike of hammer 272 is supplied from the computer 222 on line 249 to drive circuit 274. Similarly, energization of pressure rollers 252 is controlled by computer 222 over line 248 to drive circuit 258. The indexing of motor 133 is also controlled by computer 222 over line 250 to drive circuit 256.

I/O expander 242 receives in addition to the command information from computer 222 for controlling decades 261-263 on read/write data line 244, position information indicating the printing position of a respective decade from the respective decade on lines 276. This information is conveyed to the computer on read/write data line 244. A program (PROG) or clock signal from computer 222 controls the read/write data transfer on line 244. The I/O expander 242 in accordance with the data transfer on lines 244 provides the drive signals on lines 266 from drive circuits 254 for selecting indicia on decades 261-263 or a blanking signal on lines 271. Information of the blanking position of the decades is determined by the signal on the blanking lines 267.

The third decade 263 of printer 200 also includes the Kirby-Bauer indicia "N", "S", "I", "R". Signals which indicate which indicia is in the printing position of decade 263 are supplied to I/O expander 242 on lines 278 and the command signal for selecting the desired indicia on decade 263 to be printed is fed from computer 222 to decade 263 on line 266 via the drive circuit 254. Data transfer between the I/O expander and computer proceeds on the read/write data line 244.

The system 100 operates in conjunction with card 104 and carousel container 102 to test the effect of certain drugs on a bacteria sample as follows. Container 102 is supplied with the cupules 120 (except the control and reference cupules) filled with drugs, and a cultured bacteria sample is introduced into the container as described above. Thereafter the container 102 is inserted into the system 100 so that indexing arm 132 engages keyway 130 of the container. The appropriate card 104 corresponding to container 102 is inserted into the reader 180. The appropriate code is encountered and the presence of the card in the reader is detected by computer 222.

The signal is processed and the computer provides a digital signal on line 248 to drive circuit 258 to energize the advance solenoid L2, which advances the card until it engages "Home" switch 232. At this time the logic signal on line 238 to the computer is changed. This information (change in logic signals) is processed by the computer and the logic signal on line 248 to drive circuit 258 for the advance solenoid L2 is changed to cause de-energization of the advance solenoid L2. The advance of the card is thus stopped upon activation of the "Home" switch 232. The first listed item on the card, i.e., "Control" is then read, the computer causing the analog inputs 205-207 for the card reader 180 to be addressed on line 228 for multiplexing and conversion to digital form by the A to D converter 210. The card reader 180 provides analog signals to the A to D converter 210 which are proportional to the amount of light detected by the diode dectors 194, 196, 198 and these signals are converted to digital form and supplied to the computer 222 on data line 223. Thus, the darkened spaces in columns 112B and 112C to the right of "Control" are detected by computer 222 which then causes the A to D converter to be addressed via line 227 for multiplexing and digital conversion of other analog inputs. Specifically, the position of container 102 must be determined relative to the photometric reader 149 and accordingly the analog input 212 of the position reader 162 is addressed next for multiplexing and conversion to digital form. If the container 102 is situated so that the first two cupules are in a position to be read by the photometric reader 149, the computer will cause the analog inputs 217-218 for the photometric reader 149 to be addressed for multiplexing and conversion to digital form. Otherwise, a logic signal will be provided on line 250 to drive circuit 256 for the motor 133. This will energize the motor 133 causing indexing of the container 102 until it is situated so that the first two cupules are in a position to be read by the photometric reader 149.

Upon addressing of analog inputs 217 and 218 of the photometric reader 149, signals proportional to the light transmitted through cupules 1 and 2 will be provided to the A to D converter 210, converted to digital form and supplied to computer 222 over data line 223. Since cupules 1 and 2 contain only bacteria, the readings will be used as reference readings and this information is stored in computer 222. No printing is caused upon reading of cupules 1 and 2 and thereafter the computer provides a logic output signal on line 248 to cause the card advance solenoid L2 to be energized and the card to be advanced for reading columns 112A, 112B, 112C to the right of "Penicillin".

The computer 222 next provides an address signal on address line 228 for multiplexing and converting analog inputs on lines 205-207 of card reader 180 to digital form. The information is supplied in digital form to computer 222 on data line 223 and processed to determine which cupules are to be next positioned for reading by photometric reader 149. For the card 104 shown in FIG. 8, the analog input 212 of the position reader 162 is multiplexed and a logic signal output provided on line 250 from the computer to energize motor 134 and index the container so that cupules 3 and 4 are positioned for reading. The next addressed signal from computer 222 on address line 228 multiplexes the analog inputs 217 and 218 so that the photometric readings of cupules 1 and 2 are provided in digital form on data line 223 to computer 222. Still no printing occurs since cupule 5 has yet to be read. Further addressing by computer 222 takes place and the container is indexed so that cupule 5 may be read, the card remaining stationary. After the reading for cupule 5 has been entered into computer 222, the readings for cupules 3-5 are compared to the reference readings in computer 222. (Comparison may take place as each cupule is read or after the three cupules are read.) It is noted here that a reference is obtained for each reader 150, 151 and the respective reference for the respective reader is compared with subsequent readings for the same reader.

System 100 is now ready to print the results of the photometric tests for cupules 3-5. Information as to the printing position of decades 261-263 is provided to I/O expander 242 on lines 276. This information is in turn provided to computer 222 on the read/write data line 244. The direction of the bidirectional lines 244 is controlled by computer 222 via the PROG or clock signal on line 280. Computer 222 will determine whether it will be necessary to reposition any of decades 261-263. In accordance with the comparisons made by computer 222 and the decade position information, the computer 222 provides a digital signal on read/write data line 244 to I/O expander 242 for positioning, if necessary, decades 261-263. An appropriate logic signal on any of lines 265 from I/O expander 242 to drive circuits 254 will cause energization of a respective decade drive to cause the respective decade to rotate in conjunction with a timing signal from oscillator 270. Since three cupules are to be tested for "Penicillin" and three test results are to be printed out, none of decades 261-263 will be blanked. The I/O expander 242 will thus provide appropriate outputs from computer 222 via read/write data line 244 to cause decades 261-263 to be positioned for printing a "+" or "−" in accordance with the results processed by computer 222.

Once the selected indicia on decades 261–263 have been positioned, the computer causes the indicia on decades 261–263 to be printed on the card in spaces 110A, 110B, 110C to the left of "Penicillin" in accordance with whether the bacteria in cupules 3–5 has grown or not. The print signal is supplied on line 249 to drive circuit 274 which energizes solenoid L1 and causes the strike of hammer 272 on the decades 261–263. Thereafter, a logic signal is provided on line 248 to energize solenoid L2 and the pressure rollers 252 to advance the card for reading the next drug "Nafcillin".

Since system 100 includes two test readers 150, 151 and three concentrations of Penicillin were tested as mentioned, the testing sequence first caused the test results for two concentrations to be entered and the container was then indexed so that the test result for the third concentration was entered. After the indicia on the three decades were in position, the test results were printed. All testing and printing for the three concentrations of Penicillin proceed while the card remains stationary, the container being indexed after two concentrations were tested. After printing, the card was advanced to enter the test sequence information for the next drug.

The sequence information for the next drug "Nafcillin" proceeds in similar manner with the analog inputs 205–207 being addressed for multiplexing the signals derived from columns 112A, 112B and 112C to the right of "Nafcillin". The information is converted to digital form and supplied to the computer which provides a signal on line 250 to cause indexing of container 102 so that the next cupule, cupule 6, is in registration with reader 150. The effect of Nafcillin is read by reader 150 and the test information entered in computer 222 which causes decades 261 and 263 to be blanked and the proper indicia on decade 262, i.e., "+" or "−", to be positioned for printing. The computer next causes the print signal to be supplied on line 249 to cause printing in space 110B to the right of "Nafcillin" of the result of the test. Thereafter, a signal is supplied on line 248 to advance the card for reading the sequence information to the right of "Methcillin." This sequential testing under command of card 104 continues until cupule 34 is positioned and read, and the result of the test printed. Cupules 35 and 36 provide control information to complete indexing and testing of container 102, there being no hole 165 in base member 134 corresponding to the pair of cupules.

As indicated from the description above, the recorded concentration of each drug, the spaces for the printing of the test results for each drug, the drug identification, and the command information for each drug are disposed on a common line for that drug. Thus, the card reader 180 reads the command information for the drug while the card remains in the same position. After the results of the test are printed over the concentrations in columns 110A, 110B and 110C, the card is advanced. Where three concentrations are to be tested for a single drug, the procedure, as described, is to simultaneously read two cupules and index the container so that the third concentration is read. After the decades are positioned, the results are printed for the three concentrations while the card has not yet been advanced. After printing, then the card is advanced to read and print out on the next line.

For example, for Nafcillin, a single reading is taken and a single decade, decade 262, is positioned to print the "+" or "−" while the other two decades are blanked. The result for the single concentration is then printed and thereafter the card is advanced and the container indexed. Where two concentrations are to be tested, as for Kanamycin, two adjacent cupules containing the two concentrations are simultaneously read and the proper indicia for decades 262 and 263 are positioned while decade 261 is blanked. The results are then simultaneously printed over the concentrations and thereafter the card advanced and the container indexed.

The following 3-bit digital codes derived from spaces 112A, 112B, 112C provide the described testing and printing, and the indexing sequences.

000: Card is in the card reader.
010: When the card is advanced and this code is encountered, decades 261 and 263 will be blanked and the next cupule in the container will be read, compared and the proper indicia on decade 262 be positioned and printed. The card is then advanced to read the next line.
011: When the card is advanced and this code is encountered, decade 261 will be blanked and the next two cupules read, compared and the results used to position indicia on decades 262 and 263 and to print the results thereof. The card is then advanced to read the next line.
110: When the card is advanced and this code is encountered, decade 263 will be blanked and the next two cupules read, compared and the results of the test used to position indicia on decades 261 and 262. The results will then be printed and the card advanced to read the next line.
111: When the card is advanced and this code is encountered, the next three cupules will be read, compared and the test results used to position the indicia on decades 261, 262 and 263 and the results thereof printed. This is done by first reading the next two cupules, indexing the container, reading the next cupule and then positioning the indicia on decade 261–263. After the indicia on the decades have been positioned, the hammer is caused to strike and the results for the tests for the three cupules are printed.

As described, different concentrations of each drug have been tested and the test results for each concentration of each drug printed. Thus, "+'s" and "−'s" have been printed in spaces to the left of the drugs over the indicated concentration. It is thus now known whether a particular concentration of a particular drug is effective. In order to determine whether the drug itself is overall effective, the individual tests of the concentration of each drug are evaluated. One decade prints information on the effectiveness of the drug itself, i.e. the qualitative Kirby-Bauer indicia. In accordance with the results of the tests for the concentrations of each drug, the particular bacteria will be resistant to the drug, susceptible to the drug, or the testing may be indeterminant or in error. In the illustrated apparatus, qualitative tests are performed for two concentrations of a given drug and decade 263 is used to print the indicia. Thus, decade 263 will print "R" for resistant, "S" for susceptible, "I" for intermediate and "N" for nonsense (error). Decade 263 may also be blanked, if desired.

Information as to the printing position of decade 263 with respect to the qualitative indicia is provided to computer 222. This is accomplished via lines 278 to the I/O expander 242 and the read/write data line 244 between the computer and the I/O expander. As mentioned the direction of the bi-directional data lines 244 is determined by computer 222 via PROG line 280. The blank and drive signals for decade 263 are provided on lines 266 and 267 as described above.

Scoring is determined as follows.

Each test reader 150, 151 will provide separate signals to the computer for the test cells read by each. Thus, signals from test reader 150 will be identified below by the subscript "1" and signals from the reader 151 by the subscript "2". In testing three concentrations, the subscript "3" refers to reading by one of the two readers, and subscripts "1" and "3" will therefore refer to reading by the same reader 150. The two reference cells are "negative" controls. They contain inoculum only for which there will be negligible growth. $S_{c1}$ and $S_{c2}$ are the test reader outputs from the readers for the two reference cells and $S_{r1}$ and $S_{r2}$ are defined as:

$S_{r1,2} = 0.875 \, S_{c1,2}$, respectively.

The test cells contain various concentrations of drugs and the standardized bacteria sample. The first cell to be read for a particular drug contains the weakest concentration of that drug, the second a stronger concentration and the third cell contains the strongest concentration. If the drug does not kill the bacteria, it will grow in the nutrient. If the drug kills the bacteria, there will be no significant growth. The greater the growth, the weaker the signal from the test readers.

$S_{t1,2}$ are the signals from the readers for the test cells.

If $S_{t1,2} < S_{r1,2}$, respectively. Bacteria is growing and the bacteria is resistant (R) to the drug.

If $S_{t1,2} \geq S_{r1,2}$, respectively. Bacteria is not growing and there is either stasis or kill. This bacteria is susceptible (S) to the drug.

Therefore, for an individual test from an individual reader, if $S_{t1,2} < S_{r1,2}$, respectively, then score "+"; and if $S_{t1,2} \geq S_{r1,2}$, respectively, then score "−".

The overall evaluation of the drug is scored as follows:

One Cell

If:
$S_{t1} < S_{r1}$, score "+" and "R";
$S_{t1} \geq S_{r1}$, score "−" and "S".

Two Cells

If:
$S_{t1} < S_{r1}$, $S_{t2} < S_{r2}$, score "+", "+" and "R";
$S_{t1} \geq S_{r1}$, $S_{t2} \geq S_{r2}$, score "−", "−" and "S";
$S_{t1} < S_{r1}$, $S_{t2} \geq S_{r2}$, score "+", "−" and "I";
$S_{t1} \geq S_{r1}$, $S_{t2} < S_{r2}$, score "−", "+" and "N".

Three Cells

If:
$S_{t1}$, $S_{t2}$, $S_{t3} < S_{r1}$, $S_{r2}$, $S_{r3}$, respectively, score "+", "+", "+" (and "R" can be scored);
$S_{t1}$, $S_{t2}$, $S_{t3} \geq S_{r1}$, $S_{r2}$, $S_{r3}$, respectively, score "−", "−", "−" (and "S" can be scored);
$S_{t1} < S_{r1}$; $S_{t2}$, $S_{t3} \geq S_{r2}$, $S_{r3}$, respectively, score "+", "−", "−" (and "I" can be scored);
$S_{t1}$, $S_{t2} < S_{r1}$, $S_{r2}$, respectively, $S_{t3} \geq S_{r3}$, score "+", "+", "−" (and "I" can be scored);
$S_{t1} < S_{r1}$; $S_{t2} \geq S_{r2}$; $S_{t3} < S_{r3}$, score "+", "−", "+" (and "N" can be scored);
$S_{t1} \geq S_{r}$; $S_{t2} < S_{r1}$, $S_{r2}$, respectively, score "−", "+", "+" (and "N" can be scored);
$S_{t1}$, $S_{t2} \geq S_{r1}$, $S_{r2}$, respectively, $S_{t3} < S_{r2}$, score "−", "−", "+" (and "N" can be scored);

The MIC for a particular drug as determined from the above tests is the lowest concentration of that drug for which a "−" was scored. As mentioned, the subscript "3" refers to readings by reader 150.

System 100 is also operative to test a fixed number of concentrations for each drug upon detection of an appropriate code on card 104. For example, upon detection of such a code, system 100 will proceed to read the two reference cells, then the two concentrations of each drug. The sequence will proceed as follows. The two reference cells will be indexed, read and the test information stored. The card and container will be indexed and the next two cells read. The test results for the two cells will be compared with the readings for the references, and the test results for the two cells printed. The card and container will then be indexed for testing the two concentrations of the next drug in the next two cupules. Printing will proceed from decades 261 and 262 for the quantitative results while decade 263 will print the qualitative test results for the drugs.

In order to provide for communication between the system and an external device such as a computer or printer, for example for transferring data from the system to the external device, the interface 300 (FIG. 9C) is provided. The interface 300 permits data to be transferred from the computer 222 to a lab computer or a line printer for checking test results, laboratory management, etc. The data line 223 from the computer 222 to the A to D converter 210 is connected to an interface circuit 302 for providing multiplexed digital data to the interface circuit 302. A lab computer 304 initiates the data transfer via line 305 and the interconnections shown in FIGS. 9A and 9C between the interface circuit 302 and the computer 222.

Specifically, the lab computer 304, via a line receiver 306 connected to interface circuit receiver data (RXD) line 308, causes a data output on line 223 to computer 222. In turn, computer 222 provides an appropriate signal to the chip select line ($\overline{CS}$) 310 of interface current 302 to enable the interface current for reading and writing data. The appropriate signals on lines 312 ($\overline{RD}$) and 314 ($\overline{WR}$) provide for reading and writing, respectively, of data. The data is transmitted to the lab computer, on (TXD) line 316 via a line driver 318 in accordance with the clock signal provided to interface 302 on clock line (CLK) 1 of computer 222. Receiving and transmitting clock pulses are counted down by divide-by-10 counter 320 and provided to interface circuit 302 on ($\overline{RXC}$) line 322 and ($\overline{TXC}$) line 324. Control data line (C/D) 326 informs the interface circuit 302 of the nature of the signal on the data line 223.

In system 100, the analog-to-digital converter 210 is National Semiconductor Part No. ADC0816; the computer 222 is Intel Part No. 8748; the input/output Expander 242 is Intel Part No. 8243; the interface circuit 302 is Intel Part No. M8251, the divide-by-10 counter is identified by No. 74L90A available from many sources, the line receiver 306 and the line driver 318 are identified by Nos. 1488 and 1489, respectively, available from many sources, and the amplifiers are National Semiconductor Part No. LM 324A.

Computer programs for computer 222, Intel Part No. 8748, can be formulated by one of skill in the art for operation in system 100 as described above.

While the system 100 has been described for analyzing bacteria reaction to drugs, it is contemplated that the system may also be utilized to identify bacteria by suitable modification of the sample characteristic determining means, the computer program and the source/record means. Additionally, system 100 has been described to turbidimetrically analyze the samples. However, it is contemplated that electrical impedance measurements and calorimetric measurements may also be utilized to analyze the samples in addition to photometric measurements such as turbidimetric and nephelometric measurements.

The advantages of the present invention as well as certain changes and modifications of the disclosed embodiments thereof will be readily apparent to those skilled in the art. It is the applicants' intention to cover by their claims all those changes and modifications which could be made to the embodiments of the invention herein chosen for the purposes of the disclosure without departing from the spirit and scope of the invention.

What is claimed is:

1. Apparatus for automatically analyzing a plurality of samples in a variable sequence when provided with a source means containing information of the analyzing sequence, said apparatus comprising:
    information sensing means for sensing information of the analyzing sequence from the source means and providing first electrical signals representative of this information;
    sample characteristics determining means for providing second electrical signals from a plurality of test cells in accordance with the characteristics of the samples;
    recording means for recording information representative of the analysis of the samples, said recording means being adapted to record such analysis information on record means;
    correlating means for providing correlation between the source means and said information sensing means and between the record means and said recording means; and
    computer circuit means for receiving said first and second signals and providing:
    signals to said correlating means for providing said correlation; and
    signals to said recording means for recording the analysis information.

2. The apparatus as recited in claim 1, wherein said sample characteristics determining means comprises photometric means for photometrically obtaining said second electrical signals, whereby said apparatus photometrically analyzes the samples.

3. The apparatus as recited in claim 2, wherein the correlating means comprises cell indexing means for providing relative movement between the photometric means and the cells, said computer circuit means providing third signals to the cell indexing means.

4. The apparatus as recited in claim 3, wherein the correlating means further comprises additional indexing means for providing relative movement between the source means and the information sensing means and between the record means and the recording means, said computer circuit means providing fourth signals to the additional indexing means.

5. The apparatus are recited in claim 1, wherein said photometric means comprises a plurality of light emitters and corresponding light detectors so that the contents of a number of cells up to the number of emitters and detectors may be simultaneously analyzed.

6. The apparatus as recited in claims 1 or 4, wherein said apparatus is adapted to being provided with a composite source/record means on which the information of the analyzing sequence is contained and on which the analysis information is recorded, said computer circuit means providing fifth signals to said recording means.

7. The apparatus as recited in claim 6 and including a sample container which is engaged by said cell indexing means and in which are adjacently disposed the plurality of cells for holding the samples, said container being positioned relative to said photometric means so that the samples in the cells are photometrically analyzed in response to said third signals in the desired sequence.

8. The apparatus as recited in claim 6, wherein said sample container is a carousel-type container having a multiplicity of cupule cells for holding individual samples arranged about the periphery of the container and said cell indexing means is operative to rotate the carousel-type container.

9. The apparatus as recited in claim 8 and comprising photoelectric means for sensing the position of a cell relative to the photometric means.

10. The apparatus as recited in claim 8 and including the source/record means which comprises a surface having the analyzing sequence information recorded thereon and spaces for recording the photometric analysis information for each sample thereon.

11. The apparatus as recited in claim 10, wherein the source/record means surface has recorded thereon the identification of each sample to be analyzed adjacent to a space on which the photometric analysis information for that sample may be recorded.

12. The apparatus as recited in claim 11, wherein said source/record means surface has the analyzing sequence information for each sample recorded thereon adjacent to the recorded sample identification.

13. The apparatus as recited in claim 12, wherein the source/record means surface has the identification of each sample and the sequence information for that sample linearly recorded thereon in juxtaposition, and the space for recording the photometric analysis for that sample linearly disposed adjacent to one of the identification and the analyzing sequence information of the respective sample.

14. The apparatus as recited in claim 13, wherein said source/record means comprises a sheet.

15. The apparatus as recited in claim 14, wherein the analyzing sequence information is disposed on the source/record sheet linearly adjacent to the sample identification.

16. The apparatus as recited in claim 15, wherein the sample identification, the spaces for the different concentrations thereof and the sequence information for each sample are linearly disposed on said sheet, the sequence information on said sheet indicating the number of concentrations to be tested and the order of testing and the printing of the results thereof.

17. The apparatus as recited in claim 16, wherein the information sensing means comprises photoelectric means operative to sense an optical sequence code from the source/record means.

18. The apparatus as recited in claim 6, wherein the recording means comprises a decade printer.

19. The apparatus as recited in claim 18, wherein said decade printer comprises a plurality of decades.

20. The apparatus as recited in claim 18, wherein the additional indexing means comprises pressure roller means for engaging the source/record means and advancing it past the decade printer.

21. The apparatus as recited in claim 18, wherein the additional indexing means comprises pressure roller means for engaging the source/record means in sheet form and advancing it past the information detecting means and the decade printer.

22. The apparatus as recited in claim 6, wherein the third, fourth and fifth signals to the cell indexing means, the additional indexing means and the recording means, respectively, are correlated by the computer circuit means so that recording of the photometric analysis information is correlated to the correct sample and the correct concentration thereof.

23. The apparatus as recited in claim 22, wherein the computer circuit means is operative to receive and process the photometric second electrical signals for the different concentrations of a same sample, compare the photometric second signals for each concentration to a reference value, and provide sixth signals indicative of whether all of the different concentrations of the same sample are greater than the reference value or not.

24. The apparatus as recited in claim 23, wherein the computer circuit means if further operative to provide said sixth signals which are indicative of whether some of the different concentrations of the same sample are greater than the reference value or not.

25. The apparatus as recited in claim 22, wherein the photometric means comprises a plurality of light emitters and corresponding light detectors so that the contents of a number of cells up to the number of emitters and detectors may be simultaneously analyzed and wherein said recording means comprises a decade printer including a number of decades equal to the maximum number of concentrations of a sample to be analyzed, a different decade being assigned for printing the photometric analysis information for each concentration.

26. The apparatus as recited in claim 25, wherein the decade printer comprises three adjacently disposed decades adapted to print in linearly, juxtaposed spaces disposed on the source/record means, whereby recording of the photometric analysis information of each concentration of a particular drug may be printed adjacent to the identification of the drug.

27. The apparatus as recited in claim 26, wherein the photometric means comprises two light emitters and two corresponding light detectors.

28. The apparatus as recited in claim 6, wherein the apparatus is operative to advance the source/record means after all the concentrations of a sample are analyzed and after the photometric analysis information for all concentrations of that sample are recorded.

29. Apparatus for automatically analyzing a plurality of samples in a variable sequence comprising:
information sensing means for sensing information of the analyzing sequence and providing first electrical signals representative of this information, said information sensing means being adapted to sense such sequence information from a source means;
sample characteristics determining means for providing second electrical signals in accordance with the photometric analyses of the samples from a plurality of test cells;
an analog to digit converter coupled to the information sensing means and the sample characteristic determining means and being adapted to receive said first and second electrical signals and provide outputs in digital form in response thereto;
computer circuit means coupled to said analog to digital converter and being adapted to receive digital signals from said analog to digital converter representative of said first and second electrical signals;
recording means electrically coupled to said computer circuit means for recording information representative of the analysis of the samples, said recording means being adapted to record said analysis information on record means; and
correlating means for correlating said information sensing means, the source means, said sample characteristics determining means, said recording means and the record means.

30. The apparatus as recited in claim 29, wherein said sample characteristics determining means comprises photometric means for photometrically obtaining said second electrical signals, whereby said apparatus photometrically analyzes the samples.

31. The apparatus as recited in claim 30, wherein said correlating means comprises cell indexing means electrically coupled to said computer circuit means for providing relative movement between said photometric means and the cells.

32. The apparatus as recited in claim 31, wherein said correlating means further comprises additional indexing means electrically coupled to said computer circuit means for providing relative movement between the source means and said information sensing means and between the record means and said recording means.

33. The apparatus as recited in claims 29 or 32, wherein said apparatus is adapted to being provided with a composite source/record means on which the information of the analyzing sequence is contained and on which the analyses information is recorded.

34. The apparatus as recited in claim 33, wherein said recording means comprises a printer.

35. The apparatus as recited in claim 34, wherein said analog to digital converter is a time-multiplexed analog to digital converter and wherein said computer circuit means is adapted to provide address signals to the analog to digital converter to provide for multiplexing of said first and second electrical signals.

36. The apparatus as recited in claim 35, wherein said computer circuit means includes input/output expander circuit means.

37. The apparatus as recited in claim 35 and comprising photoelectric means electrically coupled to said analog to digital converter for sensing the position of a cell relative to the photoelectric means.

38. The apparatus as receited in claim 34 and including the source/record means which comprises a sheet having the analyzing sequence information recorded thereon and spaces for printing the photometric analysis information for each sample, the sheet also having printed thereon the identification of each sample to be analyzed adjacent to the space on which the photometric analysis information for that sample is to be printed.

39. The apparatus as recited in claim 29 and comprising interface means for interfacing said analog to digital converter and said computer circuit means with an external device whereby information may be transferred between said system and said external device.

40. A method for automatically analyzing a plurality of samples in a variable sequence comprising the steps of:
sensing information of the analyzing sequence from source/record means;

analyzing the contents of a plurality of test cells correlated in accordance with the sensed analyzing sequence information;

correlating the analysis results in accordance with the sensed analyzing sequence information; and recording the results of the analysis of each test cell on said source/record means in correlation with the the analysis conducted thereon.

41. The method as recited in claim 40, wherein the contents of the test cells are photometrically analyzed.

42. The method as recited in claim 41 and including the step of indexing a plurality of test cells to position the cells for photometric analysis in accordance with the sensed analyzing sequence information.

43. The method as recited in claim 42 and including the step of indexing the record means for recording the analysis results thereon in accordance with the sensed analyzing sequence information.

44. The method as recited in claim 40 or 43, wherein the analyzing sequence information is for analyzing the effect of a plurality of drugs in a plurality of concentrations thereof on a bacteria sample and said analysis information is recorded on said source/record means adjacent an identification of the respective drug disposed on the source/record means.

45. A method for automatically photometrically analyzing a plurality of samples in a variable sequence comprising the steps of:

sensing information of the analyzing sequence from source/record means and providing first electrical signals representative of this information;

photometrically obtaining second electrical signals from a plurality of test cells in accordance with the photometric characteristics of the samples;

supplying the first and second electrical signals to computer circuit means and providing third electrical signals for indexing said samples and fourth electrical signals for moving the source/record means relative to recording means as determined by the first signals, and providing fifth signals to the recording means for recording the photometric analysis information in accordance with the first and second electrical signals.

* * * * *